US012588692B2

(12) United States Patent
Saito

(10) Patent No.: US 12,588,692 B2
(45) Date of Patent: Mar. 31, 2026

(54) FEED PRODUCTION DEVICE, FEED PRODUCTION METHOD, AND FEED DEVICE

(71) Applicant: QUABIT INC., Kawaguchi (JP)

(72) Inventor: Kiyofumi Saito, Kawaguchi (JP)

(73) Assignee: QUABIT INC., Saitama (JP)

( * ) Notice: Subject to any disclaimer, the term of this patent is extended or adjusted under 35 U.S.C. 154(b) by 309 days.

(21) Appl. No.: 18/285,493

(22) PCT Filed: Dec. 24, 2021

(86) PCT No.: PCT/JP2021/048220
§ 371 (c)(1),
(2) Date: Oct. 3, 2023

(87) PCT Pub. No.: WO2022/230238
PCT Pub. Date: Nov. 3, 2022

(65) Prior Publication Data
US 2024/0358044 A1     Oct. 31, 2024

(30) Foreign Application Priority Data

Apr. 30, 2021     (JP) ................................. 2021-077026

(51) Int. Cl.
| | |
|---|---|
| *A23K 50/80* | (2016.01) |
| *A01K 61/20* | (2017.01) |
| *A01K 63/04* | (2006.01) |
| *A23K 10/16* | (2016.01) |
| *A23K 10/22* | (2016.01) |
| *C02F 1/00* | (2023.01) |
| *C12M 1/00* | (2006.01) |
| *C12M 1/34* | (2006.01) |
| *C02F 103/08* | (2006.01) |

(52) U.S. Cl.
CPC .............. *A23K 50/80* (2016.05); *A01K 61/20* (2017.01); *A23K 10/16* (2016.05); *A23K 10/22* (2016.05); *C02F 1/001* (2013.01); *C12M 41/12* (2013.01); *C12M 47/20* (2013.01); *A01K 63/045* (2013.01); *C02F 2103/08* (2013.01); *C02F 2209/02* (2013.01)

(58) Field of Classification Search
CPC ........ A23K 50/80; A23K 10/16; A23K 10/22;

A23K 10/10; A01K 61/20; A01K 63/045; A01K 61/10; C02F 1/001; C02F 2103/08; C02F 2209/02; C12M 41/12; C12M 47/20; Y02A 40/81
See application file for complete search history.

(56) References Cited

U.S. PATENT DOCUMENTS

2004/0149234 A1     8/2004  Mathur

FOREIGN PATENT DOCUMENTS

| | | | |
|---|---|---|---|
| JP | 63-273426 A | | 11/1988 |
| JP | 9-205922 A | | 8/1997 |
| JP | 2015107085 A | * | 6/2015 |
| JP | 2020-198846 | | 12/2020 |
| JP | 2021-052650 A | | 4/2021 |
| KR | 10-1933072 B1 | | 12/2018 |
| WO | WO-2005070121 A2 | * | 8/2005 ............. A01K 61/00 |

OTHER PUBLICATIONS

Tsukamoto et al. Fisheries Science (2021) 87:11-29, Published online: Nov. 25, 2020. (Year: 2020).*
Aquatic Live Food. All you need to know about Copepods. Mar. 28, 2020. Obtained on Oct. 3, 2025 from WayBack Machine) URL :<https://web.archive.org/web/20200328033715/https://www.aquaticlivefood.com.au/all-you-need-to-know-about-copepods/>. (Year: 2020).*
PCT/JP2021/048220 International Search Report and Written Opinion dated Mar. 22, 2022, 7 pages—Japanese; 6 pages—English.
Microfilm of the specification and drawings annexed to the request of Japanese Utility Model Appln. No. 46078/1985 (Laid-open No. 160656/1986) (Tokyo Kyuei Co Ltd), Oct. 4, 1986 (Oct. 4, 1986), entire text, all drawings, 2 pages—Japanese; 2 pages—English.
Rearing and Aquaculture Research Letter No. 8"(Currently, Bulletins of National Research Institute of Aquaculture" "Development of feed for larval fish without using shark eggs"; Japan Fisheries Research and Education Agency, p. 20. Mar. 2019—2 pages—Japanese; 2 pages—English.

* cited by examiner

*Primary Examiner* — Erik Kashnikow
*Assistant Examiner* — Janice Y Silverman
(74) *Attorney, Agent, or Firm* — Andrew F. Young, ESQ.; Nolte Lackenbach Siegel

(57) ABSTRACT

The feed production device includes a first water tank in which bacteria and plankton are raised, and a second water tank in which the bacteria and plankton that are raised in the first water tank are annihilated to create a feed for leptocephalus.

1 Claim, 6 Drawing Sheets

FIG. 4

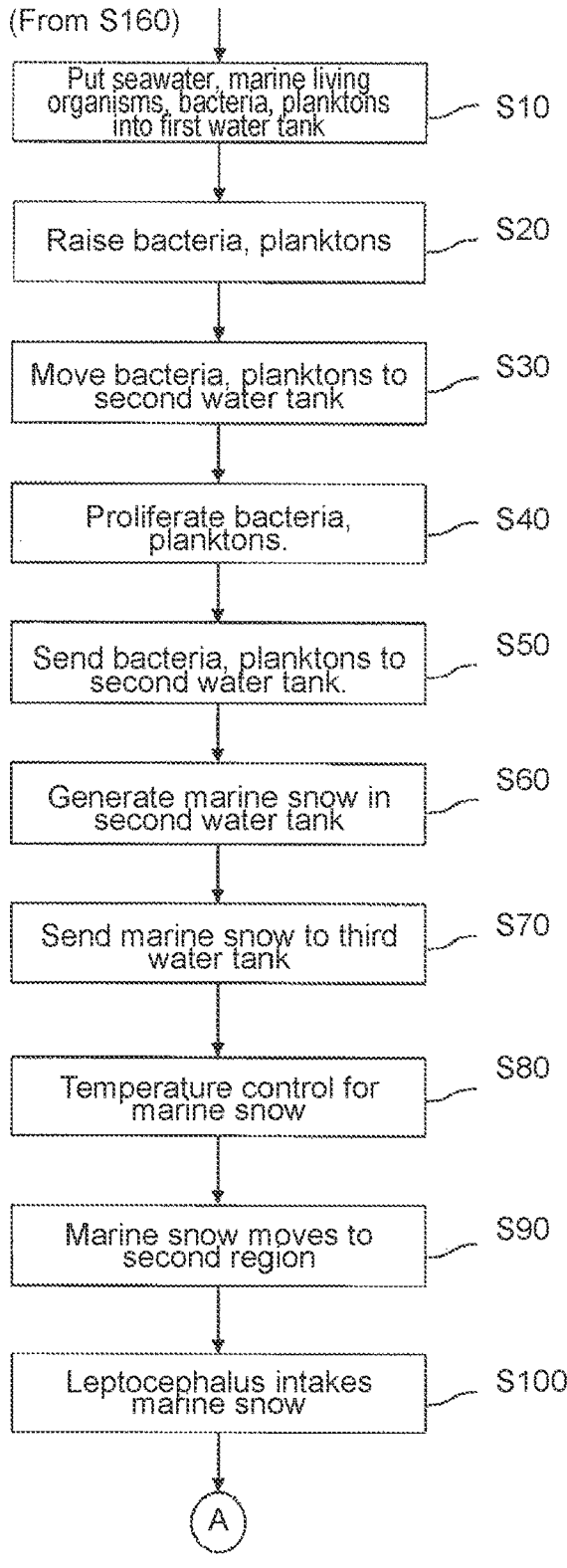

(From S160)

Put seawater, marine living organisms, bacteria, planktons into first water tank — S10

Raise bacteria, planktons — S20

Move bacteria, planktons to second water tank — S30

Proliferate bacteria, planktons. — S40

Send bacteria, planktons to second water tank. — S50

Generate marine snow in second water tank — S60

Send marine snow to third water tank — S70

Temperature control for marine snow — S80

Marine snow moves to second region — S90

Leptocephalus intakes marine snow — S100

(A)

FEED PRODUCTION DEVICE, FEED PRODUCTION METHOD, AND FEED DEVICE

CROSS REFERENCE TO RELATED APPLICATIONS

This application relates to and claims priority as a § 371 national phase, from PCT/JP2021/048220 filed Dec. 24, 2021, the entire contents of which are incorporated herein by reference, which in turn claims priority from JP 2021-077026 filed Apr. 30, 2021.

FIGURE SELECTED FOR PUBLICATION

FIG. 1

TECHNICAL FIELD

The present invention relates to a feed production device for leptocephalus, a feed production method for leptocephalus and a feed device for leptocephalus.

BACKGROUND TECHNOLOGY

An eel aqua farming, which has been carried out since the Meiji era period (in Japan), has been dramatically developed in accordance with improvements of artificial feeds and aqua farming technologies. As a result, more than 99.5% of eels consumed in Japan are aqua farming eels, which are glass eels (young eels) caught in the field and then being fed in a pond.

On the other hand, the number of Japanese eels (*Anguilla japonica*) continuously decreases since around 1970 and is currently only approximately 5% of 1960s. The overfishing of glass eels and adult eels, worsening of river environments, and changes of marine environments due to such as global warming and climate change can be considered as the reasons of decreasing Japanese eels.

Accordingly, a method for artificially producing (raising) glass eels has been studied. So far, it has been successful that glass eels that are artificially produced are fed to produce the second-generation larvae (eel leptocephalus), but the production of a number of glass eels has been failing.

The method for giving feed to eel leptocephalus must be improved for the mass production of glass eels. Non-patent document 1 describes feeds for leptocephalus. According to the non-patent document 1, an enrichment, which is made mainly of eggs of *Squalus acanthias*, is effective as feed for eel leptocephalus and based on such a fact, a suspension feed like slurry made mainly of eggs of shark has been developed. In addition, according to the non-patent document 1, the annual production scale of thousands of glass eels can be achieved because of the technological development.

PRIOR ART

Non-Patent Document

[Non-Patent Document 1]"Rearing and Aquaculture Research Letter No. 8" (Currently, Bulletins of National Research Institute of Aquaculture" Japan Fisheries Research and Education Agency, P. 20 Mar. 2019

ASPECTS AND SUMMARY OF THE PRESENT INVENTION

Objects to be Solved

However, the amount of resource of *Squalus acanthias* is stumbling and as a result the stable supply of feed mainly made of the shark egg is uncertain. In addition, the raising period to be the glass eel is about 150 days in the natural environment and in contrast, when the feed mainly made of shark eggs is applied for raising, the raising period to be the glass eel is longer than 200 days.

In addition, so far, the leptocephalus is being moved to the bottom of the fish tank by lighting the fish tank from above utilizing the nature of the leptocephalus, which avoids light, and encouraged to eat feeds which are deposited on the bottom of the fish tank. Accordingly, the whole space of the fish tank cannot be effectively utilized, so that it has been difficult to apply the large fish tank to the mass production of glass eels.

Followingly, the purpose of the present invention is to easily produce feed for leptocephalus, which is adequately applied to the mass production of fish larvae.

Means for Solving the Problem

A feed production device according to the aspect of the present representative Embodiment comprises a first water tank, in which bacteria and planktons are cultured, and a second water tank, in which the bacteria and the planktons cultured in the first water tank are annihilated to produce the feed for the leptocephalus.

Effects of the Present Invention

According to the present invention, the feed for leptocephalus, which is suitable for the mass production of fish larvae, can be easily produced.

BRIEF DESCRIPTION OF THE DRAWINGS

FIG. 4 is a flow-chart illustrating a feeding method for leptocephalus.

DETAILED DESCRIPTION OF THE PREFERRED EMBODIMENTS

Embodiment 1

The inventor illustrates the best mode of Embodiment of the present invention referring to FIGS. Further, the same member in all FIGS. according to the mode of Embodiment provided principally the same sign and the repeated description may be arbitrary omitted.

3

<Feeding Habit of Eel Leptocephali>

The inventor sets forth the feeding habit of eel leptocephali. The method for giving feed to eel leptocephalus must be improved for a mass production of glass eels. The body surface nutrient absorption theory, the marine snow theory, the Larvacean house theory, and the gelatinous zooplankton have been proposed to explain the feeding habit, but so far there is no strong evidence supporting the respective theories.

On the other hand, the nutritional level of eel leptocephalus now can be accurately presumed by the new method using nitrogen isotope ratio of amino acids. It becomes clear using such a method that the nutritional level of eel leptocephalus is relatively low, so that the marine snow theory is being supported as the feeding habit of eel leptocephalus.

Marine snow is known as the marine suspended solids that consist of such as wastes of planktons, dead planktons and dead bacteria and observable by eyes. Then, the inventor here in after sets forth the method of producing marine snow as a feed for leptocephalus.

<Configuration of the Feed Production Device for Leptocephalus>

Figure 1:
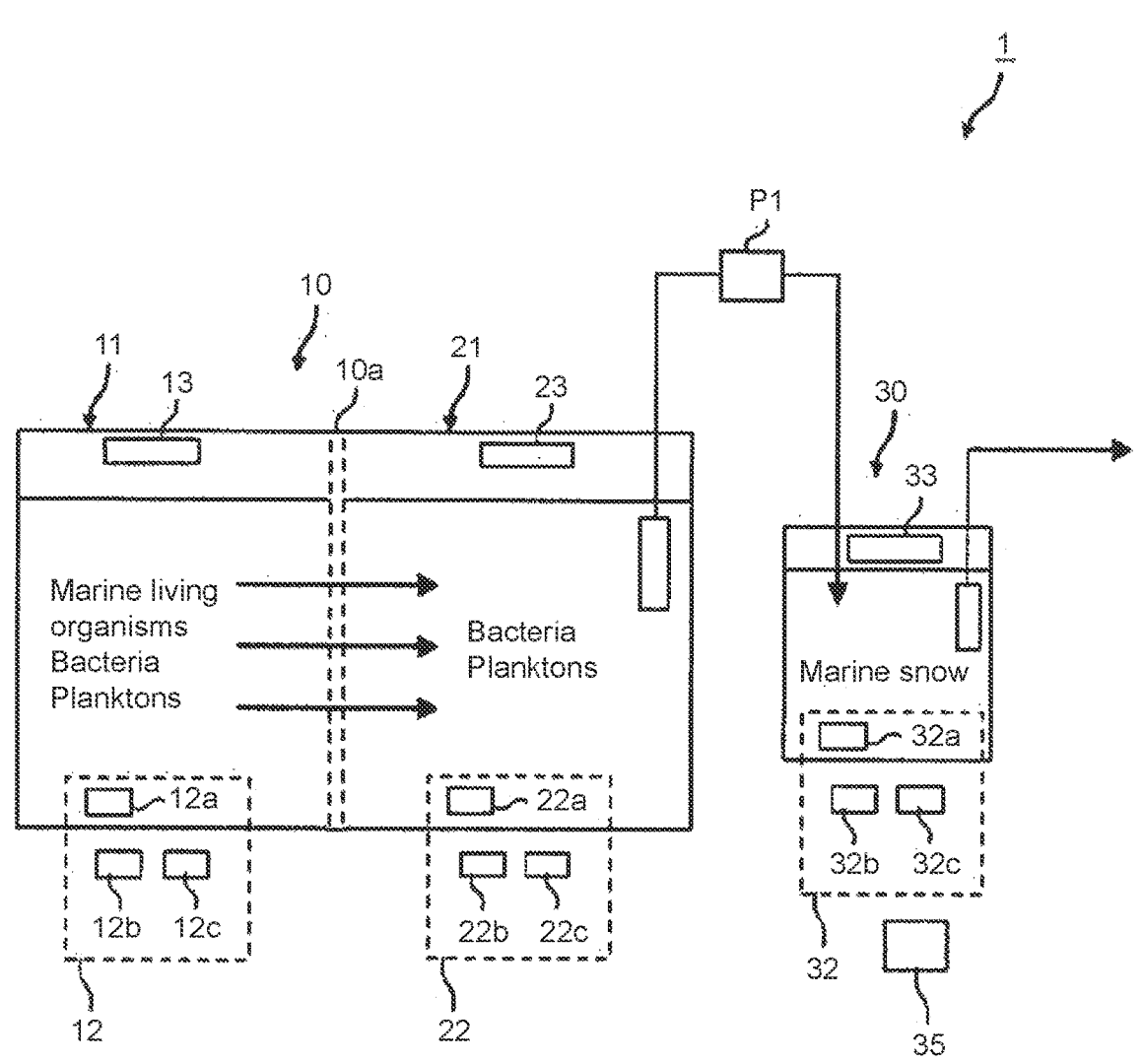
FIG. 1 is illustrating a feed production device for leptocephalus according to one aspect of Embodiment 1 of the present invention.

FIG. 1 is illustrating the feed production device for leptocephalus according to the aspect of Embodiment 1 of the present invention. Referring to FIG. 1, the feed production device 1 comprises a first water tank 10, a second water tank 30, and a pump P1.

<The First Water Tank>

The first water tank 10 is a water tank where bacteria and planktons are raised. Referring to FIG. 1, the first water tank 10 is divided to a first region 11 and a second region 21 by a partition 10a, but the partition 10a is not mandatory, wherein if the configuration thereof does not allow the living organism in the first region 11 to move into the second region 21.

<A First Region>

The first region 11 includes seawater, marine living organisms, bacteria and planktons. For example, marine living organisms include such as fish and shrimp. Bacteria grows utilizing wastes of marine living organisms as feeds. For example, bacteria may include bacteria carrying out photosynthesis such as photosynthesis bacterium and cyanobacterium and non-photosynthesis bacterium such as chemosynthetic bacterium but not limited thereto. Planktons may include plant planktons and animal planktons that carry out photosynthesis. The marine living organisms form the apex of the ecosystem of the first region.

The first region 11 comprises a temperature controller 12 and a lighting device 13. The temperature controller 12 controls temperature of seawater in the first region 11. Referring to FIG. 1, the temperature controller 12 comprises a temperature sensor 12a that measures temperature of seawater, a heater 12b that heats seawater thereof and a cooler 12c that cools seawater. The temperature controller 12 controls the heater 12b and the cooler 12c to maintain the seawater temperature to be an approximate temperature (e.g., 26±1° C. near the predetermined seawater temperature (e.g., 26° C.) based on the seawater temperature (detected seawater temperature) detected by the temperature sensor 12a. Therefore, an environment where marine living organisms, bacteria and planktons can comfortably grow, can be maintained.

In addition, a chemical substance such as ammonium, which can be the feed for bacteria, or the dead marine living organisms can be added into the first region 11 instead of the marine living organisms. However, the dead marine living organisms may deteriorate the water quality, so that the dead marine living organisms should not be added to the water tank where the live marine living organisms are therein. Further, when the marine living organisms die, the dead marine living organisms must be removed from the water tank as quickly as possible.

The temperature sensor 12a is in place in the first region 11, and the heater 12b and the cooler 12c are in place outside the first water tank 10. And seawater temperature is adjusted outside the first water tank 10 by the heater 12b and the cooler 12c, and then the temperature adjusted seawater is returned to the first region 11. In addition, the method of controlling (adjusting) temperature cannot be limited to such a method. For example, while the heater 12b is in place inside the first region 11, the cooler 12c can be in place outside the first water tank 10 to control the seawater temperature. Further, a temperature sensor can be installed to the heater 12b and the cooler 12c as well.

The lighting device 13 irradiates light (e.g., LED light) from above to the first region 11. The lighting device 13 can be in place either inside the first region 11 or outside the first region 11. When the light is irradiated to the first water tank 10, photosynthesis proceeds, so that environment, in which bacteria and plant planktons can easily grow, can be easily brought in reality. However, when the irradiation period of light is long, the large number of marine living organisms such as algae grow by photosynthesis and as a result, the ecosystem thereof can be destroyed. Accordingly, the irradiation period of light with the lighting device 13 should be controlled depending on the condition inside the first water tank 10. In addition, provided the main bacteria are bacteria such as chemical synthesis bacteria, which do not carry out photosynthesis, the lighting device 13 is not mandatory.

<A Second Region>

The second region 21 is a region where bacteria and planktons grow. The temperature controller 22 and the lighting device 23 are in place in the second region 21.

The second region 21 houses the seawater comprising bacteria and planktons moved from the first region 11. Bacteria and planktons form the apex of the ecosystem of the second region where no marine living organism exists.

The temperature controller 22 is the device that controls the seawater temperature of the second region 21. Referring to FIG. 1, the temperature controller 22 comprises a temperature sensor 22a that measures the seawater temperature, a heater 22b that heats seawater thereof and a cooler 22c that cools seawater thereof. The configuration and functions of the temperature controller 22 is the same as the temperature controller 12 of the first region 11 previously described. The temperature controller 22 controls the heater 22b and the cooler 22c to maintain the seawater temperature to be approximate temperature (e.g., 26±1° C.) near the predetermined seawater temperature (e.g., 26° C.) based on the seawater temperature (detected seawater temperature) detected by the temperature sensor 22a. The temperature controller 22 brings comfortable temperature environment for bacteria and planktons in reality, so that the growth of bacteria and planktons can be promoted.

The lighting device 23 irradiates light (e.g., LED light) to the second region 21. The configuration and functions of the lighting device 23 is the same as the lighting device 13 of the first region 11, which is previously described, so that further detail is omitted. The light is irradiated to the second region 21, so that photosynthesis in bacteria and planktons proceeds and as a result growth of bacteria and planktons can be further promoted. The seawater including the bacteria and planktons proliferated in the second region 21 is sent to the second water tank 30 using a pump P1. In addition, the second region 21 is not a mandatory configuration element and the seawater in the first region 11 can be sent to the second water tank 30.

In addition, the temperature controller 12, 22 of the first water tank 10 can be unified instead of individual units. Further, the temperature controller 12, 22 and the temperature controller 32 of the second water tank 30 can be unitarily controlled and managed with the control apparatus. Further, such a control apparatus can unitarily control the lighting devices 13, 23 and the lighting device 33 of the second water tank 30. In addition, the first region 11 and the second region 21 of the first water tank 10 can be divided into individual water tanks.

<Second Water Tank>

The second water tank 30 is the water tank in which the bacteria and planktons fed in the first water tank 10 are annihilated to generate the marine snow. The second water tank 30 comprises the temperature controller 32 and the lighting device 33.

The temperature controller 32 is the device that controls the seawater temperature in the second water tank 30. Referring to FIG. 1, the temperature controller 32 comprises a temperature sensor 32a that measures temperature of seawater, a heater 32b that heats seawater thereof and a cooler 32c that cools seawater. The configuration of the temperature controller 32 is the same as such as the temperature controller 12 described above.

The temperature controller 32 activates the heater 32b and cooler 32c to change rapidly the seawater temperature referring to the seawater temperature (detected seawater temperature) detected by the temperature sensor 32a. For example, when the standard seawater temperature is 26° C., the temperature controller 32 changes the seawater temperature higher than 15° C. in the positive direction (i.e., to be higher than 41° C.) or in the negative direction (i.e., to be lower than 11° C.) at once. Accordingly, the bacteria and planktons are annihilated by changing the seawater temperature rapidly and the marine snow including such as dead bacteria and planktons is generated.

The lighting device 33 (e.g., LED light) irradiates light to the second water tank 30. The configuration and functions of the lighting device 33 is the same as the lighting device 13 of the first region 11, which is previously described, so that further detail is omitted. When no second region 21 is in the first water tank 10, the bacteria and planktons are firstly proliferated in the second water tank 30 and then annihilated. In such a case, the bacteria and planktons can be proliferated by that the lighting device 33 irradiates light. Accordingly, when the second region 21 is in place in the first water tank 10 or the main bacteria are chemical synthesis bacteria which do not carry out photosynthesis, the lighting device 33 is not mandatory.

It is preferable that the second water tank 30 equips with a concentration measurement device 35 that measures the concentration of the marine snow. The concentration measurement device 35 irradiates light (concentration measurement light) for concentration measurement to the second water tank 30 and measures an amount of the concentration measurement light that transmits the second water tank 30. The concentration measurement device 35 measures the turbidity level of the second water tank 30 based on the measurement result of the amount of light and measures the concentration of the marine snow based on the turbidity level thereof. Accordingly, the data to control a supply amount of the marine snow can be obtained when the marine snow is sent to the water tank in which leptocephali are being fed.

The seawater containing the marine snow generated in the second water tank 30 is sent to the water tank in which leptocephali (e.g., eel leptocephali) are being fed. Therefore, the marine snow can be utilized as feed for leptocephalus.

(Method of Producing Feed for Leptocephalus)

Figure 2:
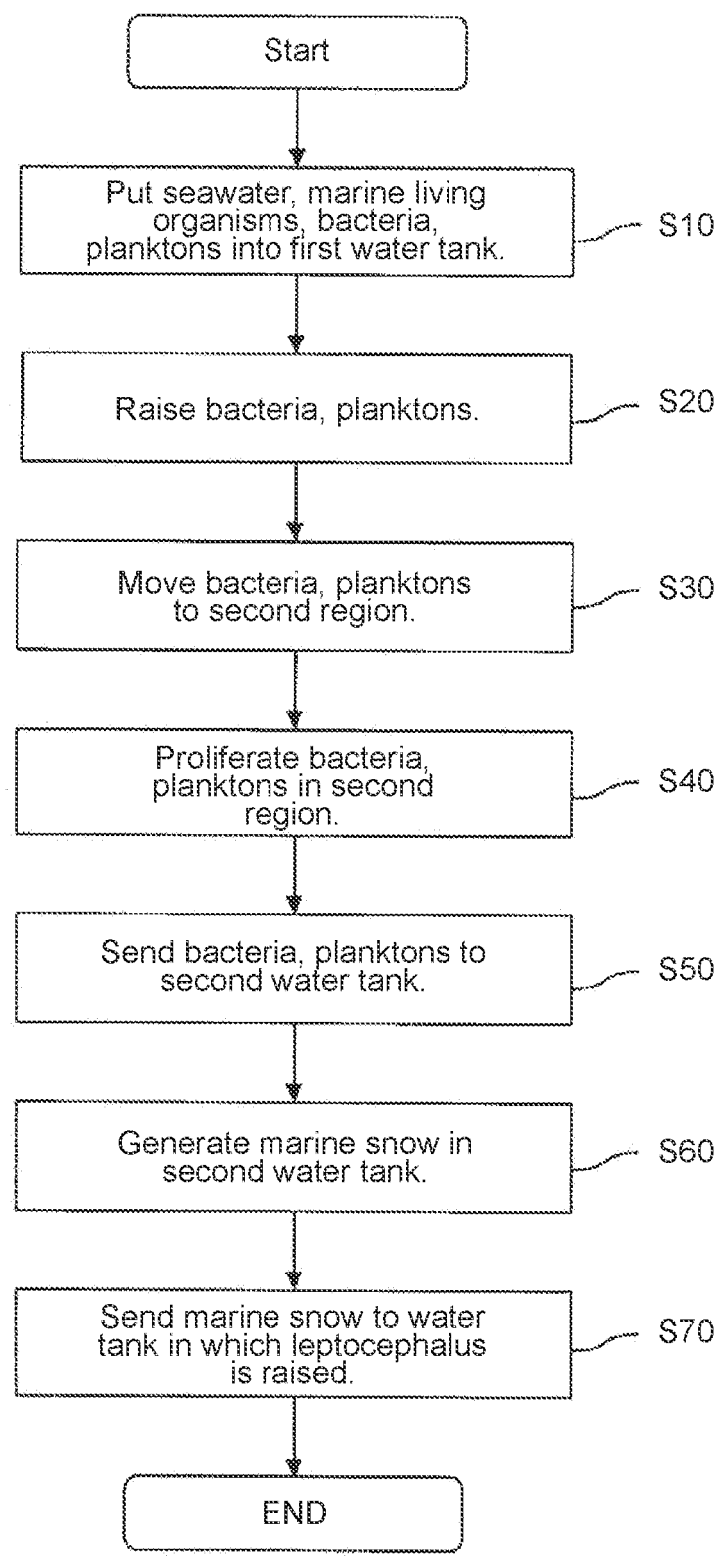
FIG. 2 is a flow-chart illustrating a feed production method for leptocephalus.

Next, the inventor sets forth the method of producing the marine snow that is a feed for leptocephalus. FIG. 2 is the flow-chart illustrating the method of producing the feed for leptocephalus.

First, the first water tank 10 is supplied with seawater at Step S10. Such seawater can be natural seawater or artificial seawater. And then, the marine living organisms, bacteria and planktons are supplied to the first region 11 of the first water tank 10. In addition, bacteria and planktons can also be supplied to the second region 21.

The bacteria and planktons are being fed in the state where the seawater temperature is being held around the predetermined seawater temperature (e.g., 26±1° C.) by the temperature controller 12 at Step S20. Further as described above, the lighting device 13 adjusts the light irradiation time period corresponding to the inside state of the first water tank 10.

The seawater including bacteria and planktons in the first region 11 moves to the second region 21 at Step S30. Such move of the seawater including bacteria and planktons occurs due to the action in which the seawater including bacteria and planktons from the first water tank 10 to the second water tank 30 is sent using the pump P1. In addition, if such as photosynthesis is not needed to grow the bacteria and planktons, Step S30 can be omitted because the second region 21 is not needed.

The bacteria and planktons grow in the second region 21 at Step S40. Light is irradiated from the lighting-imaging element 23 in the state in which the seawater temperature is being held near the predetermined seawater temperature (e.g., 26±1° C.) by the temperature controller 22. Therefore, photosynthesis is accelerated so that the bacteria such as photosynthesis bacteria and cyanobacteria and plant planktons proliferate.

The seawater containing the bacteria and planktons of the first water tank 10 is sent to the second water tank 30 by driving the pump P1 at Step S50.

The bacteria and planktons are annihilated by changing rapidly the seawater temperature of the second water tank 30 with the temperature controller 32 at Step S60. Therefore, the marine snow including the dead bacteria and planktons is generated.

The seawater including the marine snow generated at Step S60 is sent to the water tank in which leptocephali grow at Step S70. Therefore, the marine snow can be utilized as a feed for leptocephalus.

The Main Effect of the Aspect of the Present Embodiment

According to the present Embodiment, the marine snow is generated as the feed for leptocephalus by annihilating the bacteria and planktons proliferated in the second water tank 30. According to such a configuration, the feed for leptocephalus, which is suitable for mass production of fish larvae, can be easily supplied thereto.

Embodiment 2

Next, the inventor sets forth the second Embodiment. According to the present Embodiment, the inventor sets forth the leptocephalus feed device having the feed production device 1 of Embodiment 1.

<Leptocephalus Feed Device>

Figure 3:
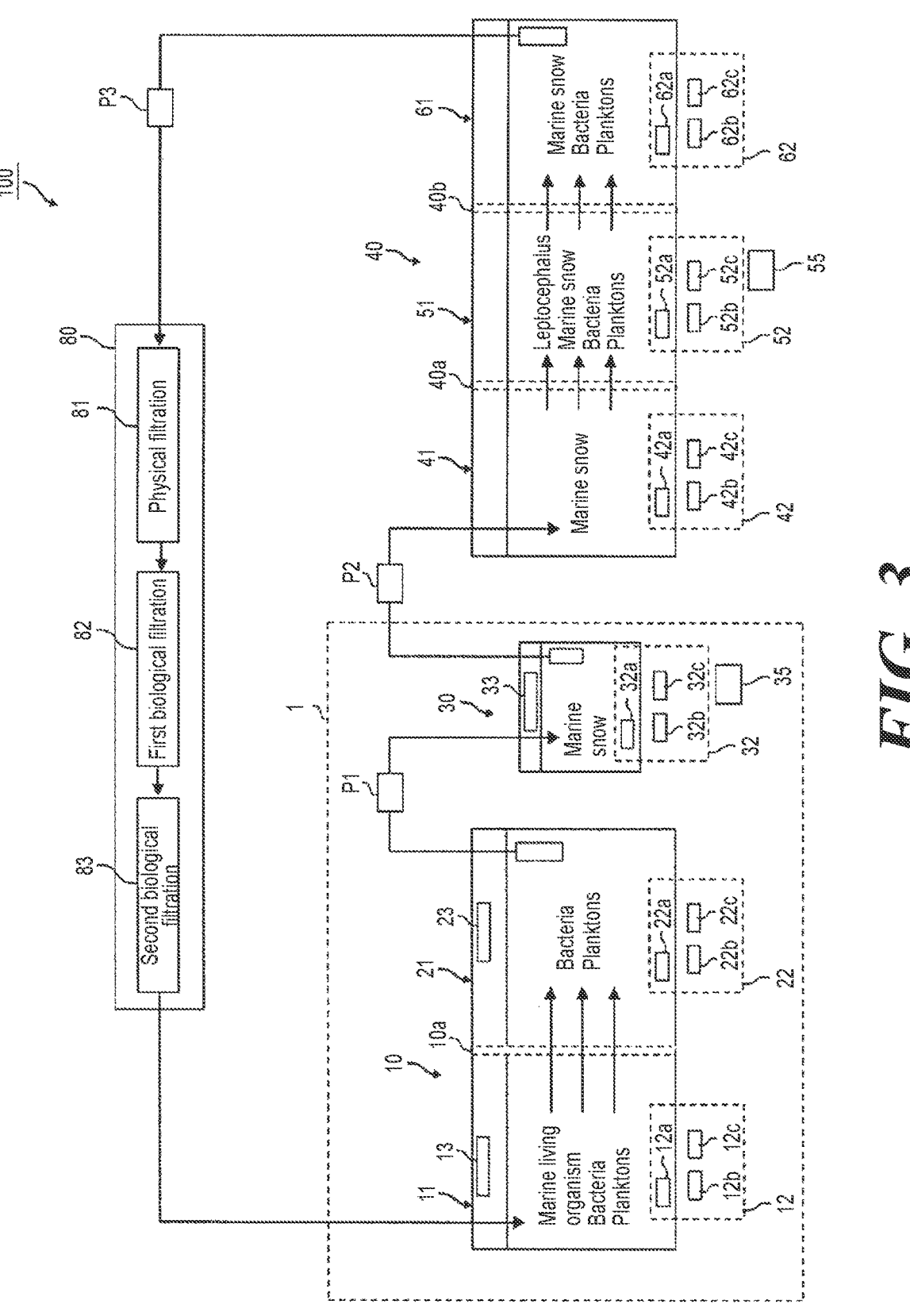
FIG. 3 is illustrating a feed device for leptocephalus according to one aspect of Embodiment 2 of the present invention.

FIG. 3 is illustrating the feed device according to Embodiment 2 of the present invention. Referring to FIG. 3, the feed device 100 comprises the feed production device 1, the third water tank 40, a filtration device 80 and the pumps P2, P3. Referring to FIG. 3, the third water tank 40 and the filtration device 80 are equipped in order in the downstream of the feed production device 1 of the feed device 100. The downstream side of the filtration device 80 connects with the first water tank 10, so that the seawater can circulate in the feed device 100.

<Third Water Tank>

The third water tank 40 is a water tank in which leptocephalus is fed with the feed that is the marine snow generated in the second water tank 30. Referring to FIG. 3, the third water tank 40 is divided to the first region 41, the second region 51 and the third region 61 with the partitions 40a, 40b. However, if the leptocephalus in the second region 51 cannot move to the first region 41 and the third region 61 due to the configuration thereof, the partitions 40a, 40b are not needed.

<The First Region>

The first region 41 is the region in which the seawater containing the marine snow generated in the second water tank 30 of the feed production device 1 is stored. The seawater containing the marine snow is sent from the second water tank 30 to the third water tank 40 using the pump P2. Temperature of the seawater containing the marine snow, which is sent from the second water tank 30, is variable. Provided such a seawater is supplied to the second region 51 in which leptocephali are being raised, temperature of the second region 51 becomes variable, the leptocephali may be impaired. Accordingly, the temperature of the seawater containing the marine snow sent from the second water tank 30 in the first region 41 should be controlled. The temperature adjusted seawater containing marine snow in the first region 41 moves to the second region 51.

The first region 41 comprises the temperature controller 42 that controls temperature of seawater in the first region 41. Referring to FIG. 3, the temperature controller 42 comprises the temperature sensor 42a, the heater 42b that heats seawater and the cooler 42c that cools seawater. The configuration and functions of the temperature controller 42 are the same as the temperature controller 12 and so on as described before. The temperature controller 42 controls the heater 42b and the cooler 42c to maintain the seawater temperature to be approximate temperature (e.g., 26±1° C. near the predetermined seawater temperature (e.g., 26° C.) based on the seawater temperature (detected seawater temperature) detected by the temperature sensor 42a. Therefore, the temperature of the marine snow can be adjusted to the seawater temperature in the fifth water tank 50 in which leptocephali are being raised. In addition, lighting is not required in the first region 41, so the installation of the lighting device is optional.

<The Second Region>

The second region 51 is the water tank in which leptocephali are raised with the marine snow as the feed supplied from the first region 41. It is a preferable environment in which no light is incident to the second region 51 because leptocephalus avoids light in nature. For example, the third water tank can be covered with light blocking material or can be set an indoor environment blocking light.

The second region 51 houses such as seawater, leptocephali and the marine snow and so forth. The second region

51 is in the state where the marine snow is floating in the seawater. The marine snow is a feed that resembles the marine floating material existing in nature, wherein the similar condition to nature is recreated in the second region 51. Leptocephalus intakes the floating marine snow and is raised until becoming a fish larva such as a glass eel.

The second region 51 comprises the temperature controller 52. The temperature controller 52 is the device that controls the seawater temperature of the second region 51. Referring to FIG. 3, the temperature controller 52 comprises the temperature sensor 52a, the heater 52b that heats seawater and the cooler 52c that cools seawater. The configuration and functions of the temperature controller 52 are the same as the temperature controller 12 and so on as described before. The temperature controller 52 controls the heater 52b and the cooler 52c to maintain the seawater temperature to be an approximate temperature (e.g., 26±1° C.) near the predetermined seawater temperature (e.g., 26° C.) based on the seawater temperature (detected seawater temperature) detected by the temperature sensor 52a. Accordingly, an environment where leptocephali and fish larvae can grow comfortably can be maintained.

It is preferable that the concentration measurement device 55 that measures concentration of the marine snow is in place in the second region 51. The concentration measurement device 55 has the same configuration as the concentration measurement device 35 as described before. The concentration measurement device 55 measures a turbidity level of the second region 51 and then measures the concentration of the marine snow. Accordingly, the environment where leptocephali can grow comfortably can be maintained.

The seawater of the second region 51 moves to the third region 61. The seawater that moves to the third region 61 includes the leftover marine snow, bacteria and planktons.

<Third Region>

The third region 61 is the region from which the seawater is sent to the outside of the third water tank 40 so that environment of the second region 51 cannot change. The seawater that has moved to the third region 61 is sent to the filtration device 80 using the pump 3.

The third region 61 comprises the temperature controller 62. The temperature controller 62 is the device that controls seawater temperature of the third region 61. Referring to FIG. 3, the temperature controller 62 comprises the temperature sensor 62a, the heater 62b that heats seawater and the cooler 62c that cools seawater. The configuration and functions of the temperature controller 62 are the same as the temperature controller 12 and so on as described before. The temperature controller 62 controls the heater 62b and the cooler 62c to maintain the seawater temperature to be approximate temperature (e.g., 26±1° C.) near the predetermined seawater temperature (e.g., 26° C.) based on the seawater temperature (detected seawater temperature) detected by the temperature sensor 62a. Accordingly, the seawater temperature in the third region 61 becomes approximately the same as the seawater temperature in the second region 51, so that an effect that affects the environment of the second region 51 can be managed.

In addition, the temperature controller 42, 52, 62 of the third water tank 40 is not required to be individual and can be formed in one unit. Further, the temperature controller 42, 52, 62 can be managed in an integrated fashion by the control device. Further, such a control device can manage and control all temperature controllers 12, 22, 32, 42, 52, 62 in an integrated fashion. In addition, the first region 41 of the third water tank 40, the second region 51 of the second region and the third region 61 of the third region can be separately placed in the respective water tanks.

<Filtration Device>

The filtration device 80 is the device that filters the seawater sent from the third water tank 40. Referring to FIG. 3, the filtration device 80 comprises a physical filtration device 81, the first biological filtration device 82 and the second filtration device 83.

The physical filtration device 81 removes impurities such as marine snow included in the seawater sent from the third water tank 40. The physical filtration device 81 comprises a chemical filter that adsorbs impurities, so that impurities can be removed from the seawater. However, seawater contains hazardous substances such as ammonia that is originated from wastes of marine living organisms despite removing impurities. Therefore, the first biological filtration device 82 carries out a process to remove hazardous substances such as ammonia.

The first biological filtration device 82 carries out nitrification of ammonia included in the seawater with an aerobic bacterium. Such an aerobic bacterium converts ammonia to a nitrite salt and further the nitrite salt to a nitrate salt. Specifically, a series of chemical reactions, in which ammonia is nitrified to the nitrate salt, is carried out in the first biological filtration device 82.

A nitrate salt is less toxic than ammonia. On the other hand, the nitrate salt is left in seawater, pH of the seawater becomes high and then the seawater turns acidic. Marine living organisms shall die in such an acidic seawater and consequently the marine snow cannot be generated. As a result, the feed cannot be supplied to leptocephalus and as a result the feed device 100 can be dysfunctional. The second biological filtration device 83 carries out removing the nitrate salt to avoid such a condition.

The nitrate salt included in the seawater is reduced to nitrogen, which is discharged into the air, by anaerobic bacteria in the second biological filtration device 83. Therefore, nitrate salts can be removed from the seawater circulating in the feed device 100. The seawater from which the nitrate salt was removed is resent to the first water tank 10. Therefore, the feed device 100 can utilize the seawater while circulating.

<Method for Raising Leptocephalus>

Figure 5:
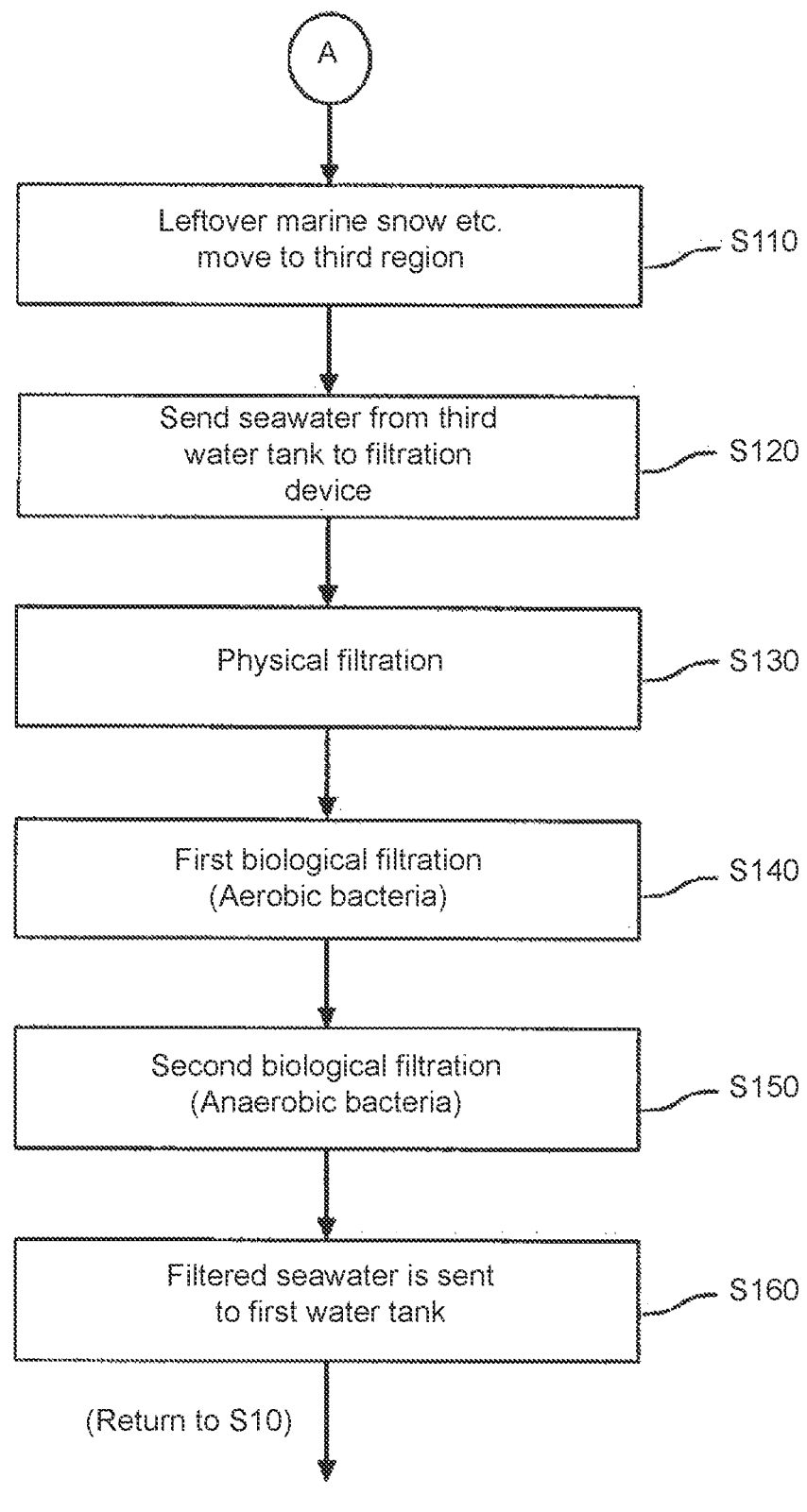
FIG. 5 is a flow-chart illustrating a feeding method for leptocephalus.

Next, the inventor sets forth a method for raising leptocephalus. FIG. 4 and FIG. 5 are flow charts illustrating the method for raising leptocephalus. Referring to FIG. 4 as well as FIG. 2, Steps of the method for raising leptocephalus are illustrated using the feed production device 1. Steps S10-S60 of FIG. 4 are approximately the same as FIG. 2.

Referring to FIG. 4, the seawater including the marine snow is sent to the third water tank 40 at Step S70. Step S70 is carried out based on the concentration of the marine snow in the third water tank 40, which the concentration measurement device 55 measures. For example, provided the concentration of the marine snow in the third water tank 40 is the same as or lower than the predetermined marine snow concentration, the process at Step S70 is carried out. In contrast, for example, given the concentration of the marine snow in the third water tank 40 is higher than the predetermined marine snow concentration, Step S70 can be skipped.

Adjustment of the seawater temperature including marine snow, which is sent to the third water tank 40, is carried out with the temperature controller 42. The temperature controller 42 adjusts the seawater temperature in the first region 41 of the third water tank 40 to be near the predetermined temperature (e.g., 26±1° C.).

The seawater including marine snow in the first region 41 moves to the second region 51. Such a move of bacteria and planktons takes place due to the action in which seawater is sent from the second water tank 30 to the third water tank 40 using the pump P2 and the action in which seawater is sent from the third water tank 40 to the filtration device 80 using the pump P3.

Leptocephalus being raised in the second region 51 of the third water tank 40 intakes the marine snow floating in the seawater at Step S100. The seawater including such as leftover marine snow moves from the second region 51 to the third region 61 at Step S110. The pump P3 is driven to send such as the leftover marine snow from the third region 61 to the filtration device 80 at Step S120.

Impurities such as marine snow included in the seawater sent from the sixth water tank 60 are removed by the physical filtration device 81 at Step S130. Specifically, the impurities are removed from the seawater by adsorbing the impurities to the chemical filter.

Ammonia included in seawater is nitrified using the first biological filtration device 82 at Step S140. Specifically, aerobic bacteria convert ammonia to nitrite salt and further converts the nitrite salt to the nitrate salt, so that a series of processes relative to nitrification of ammonia can be carried out.

The nitrate salt included in the seawater is reduced to nitrogen, which is discharged into the air, by anaerobic bacteria of the second biological filtration device 83 at Step S150. Therefore, the nitrate salt can be removed from the seawater.

The seawater filtered with the filtration device 80 is sent to the first water tank 10 at Step S160. Accordingly, the seawater can be circulated in the feed device 100. In addition, new seawater can be introduced to replace the seawater in the feed device 100 when needed. In addition, the circulation of the seawater and replacement of a part of the seawater can be carried out in parallel.

After Step S160 is over, the flow returns to Step S10. Processes from S10 to S160 should be carried out until leptocephalus grows to a fish larva (e.g., glass eel).

In addition, Step S10 after the second cycle can be arbitrary omitted. In such a case, Step S20 is carried out next to Step S160. In addition, for convenience of explanation, the explanation of each step is carried out one by one, but multiple steps are actually carried out in parallel in the feed device 100. Specifically, the respective steps (Step S10-S40) relative to raising bacteria and planktons in first water tank 10, the respective steps (Step S50-S60) relative to generation of the marine snow in the second water tank 30, and the respective steps (Step S70-S110) relative to feeding the marine snow to leptocephalus in the third water tank 40 are carried out in parallel.

The Main Effects of the Aspect of the Present Embodiment

According to the present Embodiment, the marine snow generated in the second water tank 30 is supplied to leptocephali being raised in the third water tank 40. According to such a configuration, generating the feed and raising leptocephalus using the generated feed can be carried out in a unified manner. Therefore, a mass production of fish larvae (e.g., glass eel) can be carried out by raising leptocephali.

Embodiment 3

Next, the inventor sets forth the present Embodiment 3. According to the present Embodiment, the configuration of

Figure 6:
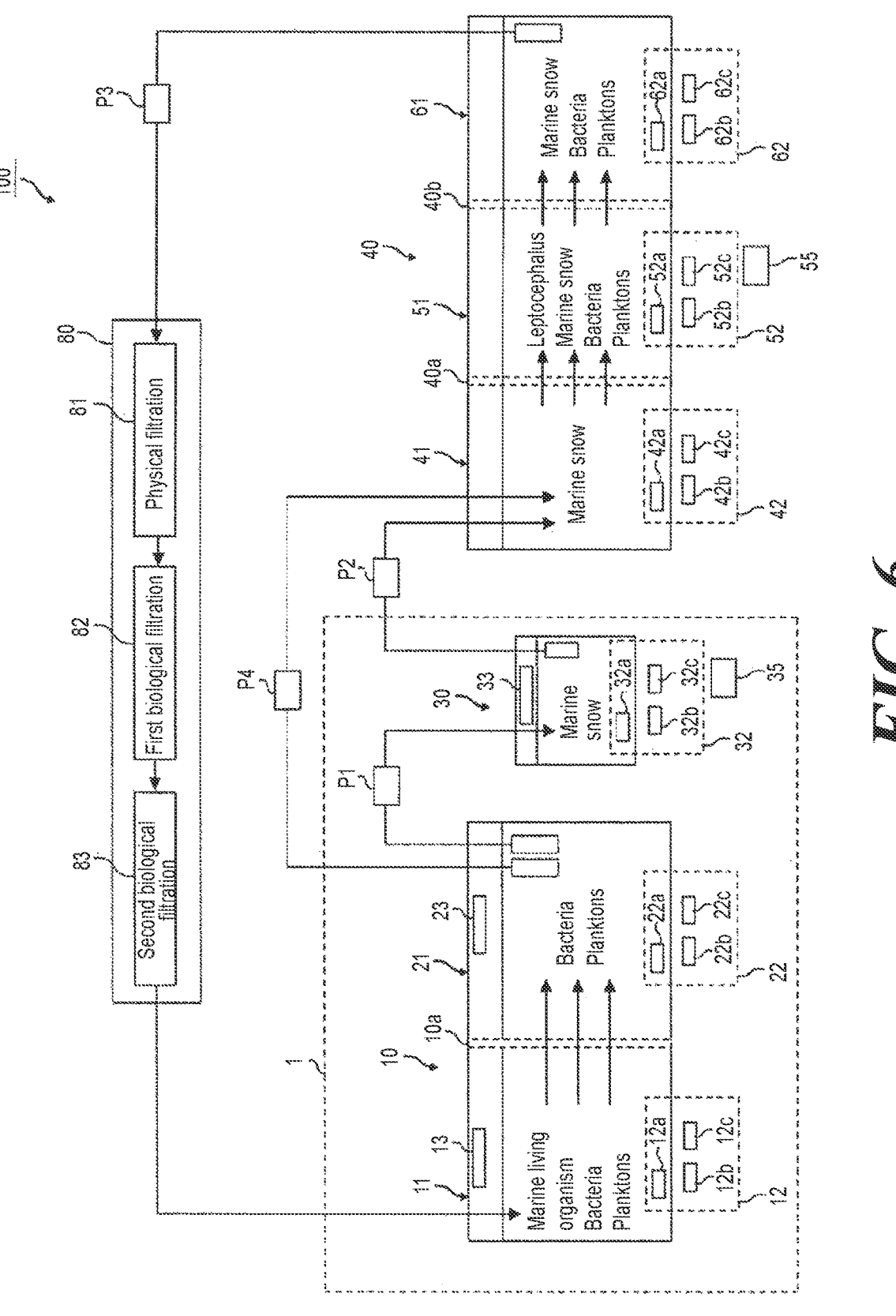
FIG. 6 is illustrating a feed device for leptocephalus according to one aspect of Embodiment 3 of the present invention.

11 the feed device for leptocephalus is different from Embodiment 2 thereof. FIG. 6 is illustrating the feed device according to Embodiment 3 of the present invention. According to the present Embodiment, the configuration, in which the pump P4 is in place between the first water tank 10 and the third water tank 40, is different from the configuration of the feed device 100 referring to FIG. 3.

As set forth before, when the concentration of the marine snow in the third water tank 30 is higher than the predetermined concentration of the marine snow, the process, in which the seawater including the marine snow is sent from the second water tank 30 to the third water tank 40, is omitted. Following, the flow of the seawater suspends, so that quality of water in the third water tank 40 can be impaired.

Then, at Step S70 according to the present Embodiment, when the seawater including the marine snow cannot be sent from the second water tank 30 to the third water tank 40, the pump P4 is driven to send the seawater in the second region 21 of the first water tank 10 to the first region 41 of the third water tank 40. Therefore, the flow of the seawater does not suspend, so that impairment of the quality of water in the third water tank 40 can be prevented.

Further, the present invention is not limited to the aspect of Embodiments described above and a variety of alternative Embodiments can be included. For example, the aspect of Embodiment described above is described in detail to explain the present invention, but it may not include all configurations set forth above.

In addition, one element of the configuration of the aspect of one Embodiment can be replaced with the other aspect of another Embodiment or the configuration of an alternative Embodiment. In addition, a configuration of the other Embodiment can be added to one aspect of Embodiment. Further, the relative scale of each element described in FIGS. is simplified or ideal to easily explain the present invention, but it may be more complicated in an actual application.

REFERENCE OF SIGNS

1 Feed production device
10 First water tank
12, 22, 32, 42, 52, 62 Temperature controller
13, 23, 33 Lighting device
30 Second water tank
35, 55 Concentration measurement device
40 Third water tank
80 Filtration device
81 Physical filtration device
82 First biological filtration device
83 Second biological filtration device
100 Feed device

What is claimed is:
1. A feed production method comprising conducting the steps of:
i) providing a feed device further comprising:
a first water tank containing seawater in which marine living organisms, bacteria and planktons are raised;
said first water tank is partitioned into a first region and a second region and said partition not allowing said marine living organisms to move into said second region;
said marine living organisms are an apex of an ecosystem in said first region, and said bacteria and said planktons are an apex of an ecosystem in said second region where there are no marine living organisms; and
a first region temperature controller maintaining a temperature of said seawater in said first region at a predetermined seawater temperature where said marine living organisms, bacteria and planktons are maintained;
said first region temperature controller having a seawater temperature sensor in place within the first region of said first water tank and a seawater heater and a seawater cooler in place outside the first water tank;
a first region lighting device in said first region so that a first region photosynthesis in said bacteria and planktons is promoted;
a second region temperature controller maintaining a temperature of said seawater in said second region at said predetermined seawater temperature where said bacteria and planktons are promoted;
said second region temperature controller having a seawater temperature sensor in place within said second region of said first water tank and a seawater heater and a seawater cooler in place outside said first water tank;
a second region lighting device in said second region so that a second region photosynthesis in said bacteria and planktons is promoted;
a second water tank containing seawater in a first pumped flow from said second region of said first water tank and that generates a feed for leptocephalus by annihilating said bacteria and said planktons that are raised in said second region of said first water tank and received in said second water tank for annihilation;
a second water tank temperature controller controlling a temperature of said seawater in said second water tank at a predetermined seawater temperature;
said second water tank temperature controller having a seawater temperature sensor, a seawater heater outside said second water tank, and a seawater cooler outside said second water tank;
said second water tank temperature controller controlling said seawater heater and said seawater cooler and annihilating said bacteria and said planktons in said second water tank by changing said seawater temperature;
a third water tank containing seawater in a second pumped flow from said second water tank, wherein leptocephalus are raised by feeding with a feed comprising the annihilated bacteria and said annihilated planktons pumped from said second water tank;
a filter device that filters seawater received from said third water tank in a third pumped flow between said third water tank and said first region of said first water tank;
ii) raising bacteria and planktons in said first region of said first water tank by operating said first temperature controller at said initial step to maintain said predetermined seawater temperature in said first region and by operating said first region lighting device and promoting said photosynthesis in said bacteria and planktons;
iii) partitioning said first water tank into said first region and said second region, preventing said marine living organisms from moving into said second region;

iv) raising bacteria and planktons in said second region of said first water tank by operating said second temperature controller to maintain said predetermined seawater temperature in said second region and by operating said second region lighting device and promoting said photosynthesis in said bacteria and planktons;

v) operating said first pumped flow to move seawater from said second region of said first water tank to said second water tank;

vi) receiving in said second water tank said seawater from said second region of said first water tank containing said bacteria and said planktons;

vii) generating, in said second water tank, said feed for leptocephalus by annihilating in said second water tank said bacteria and said planktons that are raised in said first water tank;

wherein said step of generating, in said second water tank, includes the second step of controlling said second water tank temperature controller in said second water tank to control said seawater heater and said seawater cooler and changing the seawater temperature detected by said seawater temperature sensor and annihilating said bacteria and said planktons in said second water tank by changing said seawater temperature and generating said feed;

viii) moving said feed by said second pumped flow from said second water tank to said third water tank and raising said leptocephalus by feeding with said feed;

ix) filtering a seawater in said third pumped flow from said third water tank to said first region of said first water tank.

\* \* \* \* \*